(12) United States Patent  (10) Patent No.: US 9,177,457 B2
Shin et al.  (45) Date of Patent: Nov. 3, 2015

(54) ELECTRONIC DEVICE FOR PROVIDING CONTENT ACCORDING TO USER'S POSTURE AND CONTENT PROVIDING METHOD THEREOF

(71) Applicant: SAMSUNG ELECTRONICS CO., LTD., Suwon-si (KR)

(72) Inventors: Dong-yun Shin, Seongnam-si (KR); Youn-gun Jung, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 13/953,919

(22) Filed: Jul. 30, 2013

(65) Prior Publication Data

US 2014/0028458 A1   Jan. 30, 2014

(30) Foreign Application Priority Data

Jul. 30, 2012  (KR) .................. 10-2012-0083508

(51) Int. Cl.
G08B 23/00 (2006.01)
G08B 21/02 (2006.01)
A61B 5/00 (2006.01)
A61B 5/107 (2006.01)

(52) U.S. Cl.
CPC .............. *G08B 21/02* (2013.01); *A61B 5/0077* (2013.01); *A61B 5/4561* (2013.01); *A61B 5/486* (2013.01); *A61B 5/1079* (2013.01); *A61B 5/6891* (2013.01); *A61B 5/6898* (2013.01)

(58) Field of Classification Search
CPC .... G08B 21/02; A61B 5/0077; A61B 5/4561; A61B 5/486; A61B 5/6891; A61B 5/6898; A61B 5/1079

USPC .......... 340/575, 573.1, 573.7, 574, 540, 500; 345/10; 348/61, 77, 78, 169; 600/595, 600/301

See application file for complete search history.

(56) References Cited

U.S. PATENT DOCUMENTS

| 8,022,981 | B2 | 9/2011 | Yoo et al. |
| 8,810,413 | B2* | 8/2014 | Wong et al. .................. 340/575 |
| 2008/0294018 | A1 | 11/2008 | Kurtz et al. |
| 2010/0022351 | A1 | 1/2010 | Lanfermann et al. |
| 2010/0045469 | A1* | 2/2010 | Reijndorp et al. ......... 340/573.7 |
| 2010/0081475 | A1* | 4/2010 | Chiang et al. ................. 455/564 |

(Continued)

FOREIGN PATENT DOCUMENTS

JP   2012-066026 A   4/2012
KR   10-0430840 B1   5/2004

(Continued)

OTHER PUBLICATIONS

Communication dated Oct. 28, 2013, issued by the European Patent Office in corresponding Application No. 13177857.3.

(Continued)

*Primary Examiner* — Anh V La

(74) *Attorney, Agent, or Firm* — Sughrue Mion, PLLC

(57) ABSTRACT

A content providing method in an electronic device includes reproducing an image of content; obtaining information regarding a posture of a user based on an image of the user; determining whether the posture of the user is acceptable based on the obtained information regarding the posture of the user; and controlling reproduction of the content according to a result of the determination.

37 Claims, 13 Drawing Sheets

(56) References Cited

U.S. PATENT DOCUMENTS

2011/0072457 A1\* 3/2011 Lanfermann et al. ........... 725/34
2011/0275939 A1 11/2011 Walsh et al.
2012/0076428 A1 3/2012 Yokono et al.

FOREIGN PATENT DOCUMENTS

| KR | 10-2005-0040307 A | 5/2005 |
|---|---|---|
| KR | 10-2011-0134737 A | 12/2011 |
| KR | 10-2012-0078462 A | 7/2012 |
| WO | 2010/095035 A1 | 8/2010 |

OTHER PUBLICATIONS

International Search Report (PCT/ISA/220) dated Nov. 11, 2013, issued in corresponding Application No. PCT/KR2013/006574.
Written Opinion (PCTISA237) issued Nov. 11, 2013, in corresponding International Application No. PCT/KR2013/006754.
Jaimes et al., Sit Straight (and tell me what I did today): A Human Posture Alarm and Activity Summarization System, FXPAL Japan, Corporate Research Group, Fuji Xerox Co., Ltd., ACM, Nov. 11, 2005, 12 total pages.

\* cited by examiner

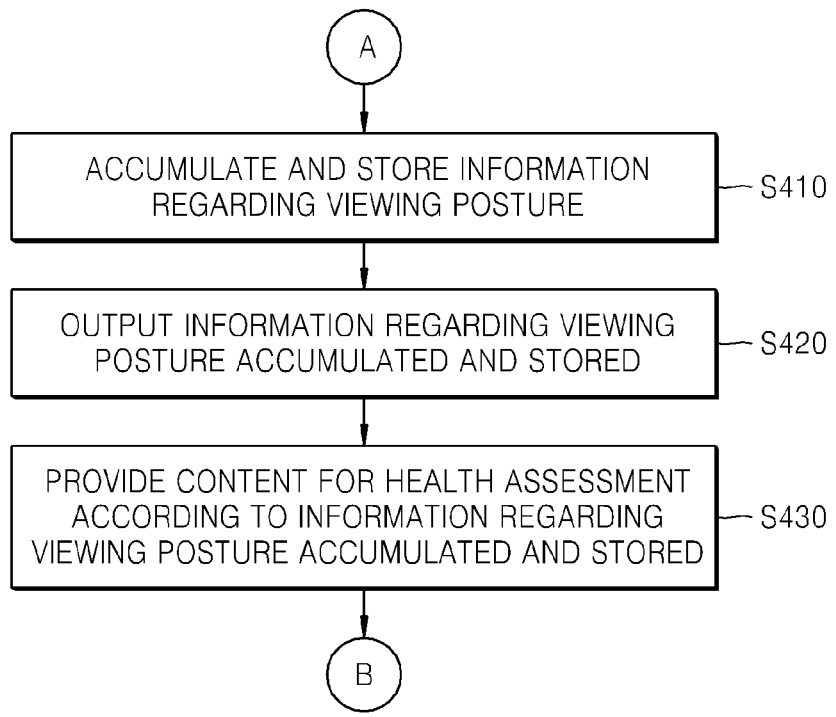
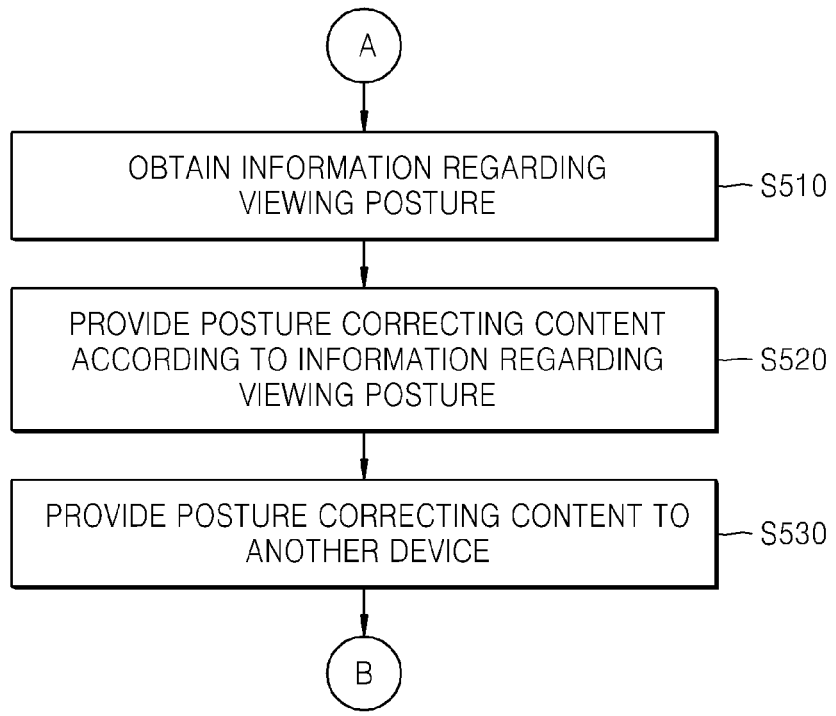

FIG. 10
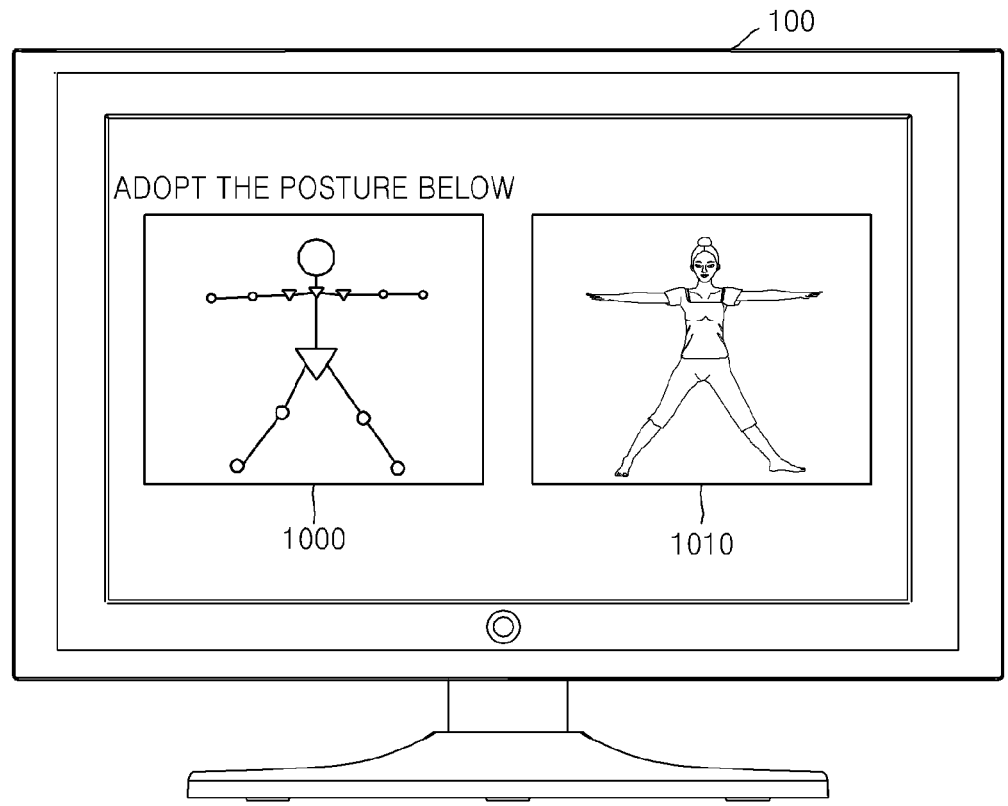
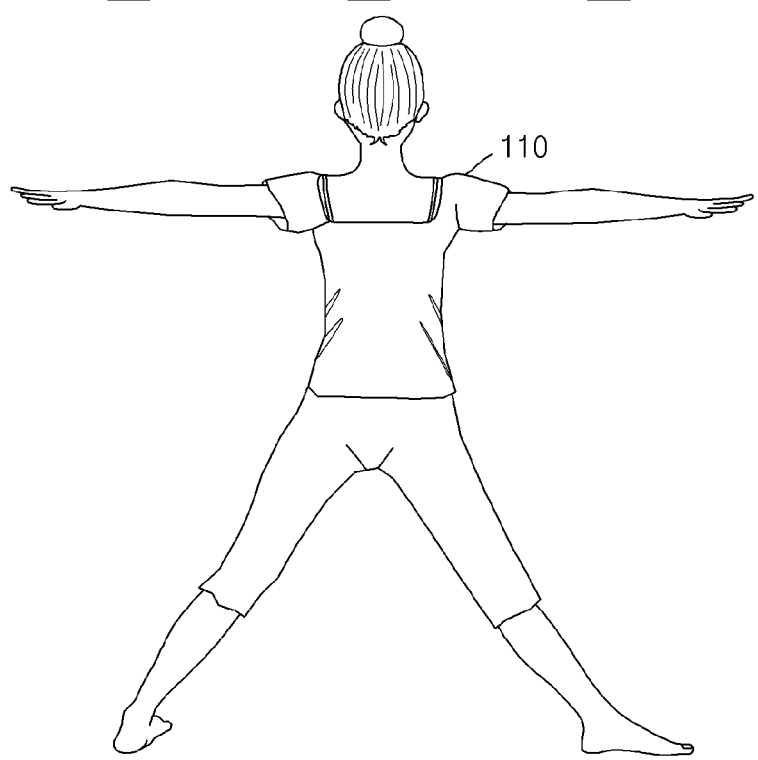

ELECTRONIC DEVICE FOR PROVIDING CONTENT ACCORDING TO USER'S POSTURE AND CONTENT PROVIDING METHOD THEREOF

CROSS-REFERENCE TO RELATED PATENT APPLICATION

This application claims priority from Korean Patent Application No. 10-2012-0083508, filed on Jul. 30, 2012, in the Korean Intellectual Property Office, the disclosure of which is incorporated herein by reference in its entirety.

BACKGROUND

1. Field

Apparatuses and methods consistent with exemplary embodiments relate to an electronic device that provides content according to a user's posture and a content providing method thereof, and more particularly, to an electronic device that provides content according to a users posture based on a captured image of the user so that the user may correct his or her posture, and a content providing method thereof.

2. Description of the Related Art

Demands for providing image contents or other contents through televisions (TVs), tablet personal computers (PCs), Internet PCs or the like have rapidly increased. In addition, as a user spends increased time watching such contents, it is desirable to protect the users health by displaying information to assist the user in correcting his or her posture when watching the contents.

In particular, in a case of infants or small children, there is a higher need for providing content in a way such that the infants or the small children may stay in a correct posture.

In addition, although methods and apparatuses for detecting a body posture from an image have been developed, methods and apparatuses for inducing a correct posture of a user who watches content have not been provided.

SUMMARY

One or more exemplary embodiments provide an electronic device which controls content that is provided to the user according to a user's posture in an image captured while the user watches the content so that the user may have a correct posture, and a content providing method thereof.

One or more exemplary embodiments also provide an electronic device which is capable of obtaining information regarding a users posture based on an image of the user and providing content for correcting the users posture, and a content providing method thereof.

According to an aspect of an exemplary embodiment, there is provided a content providing method in an electronic device, the method including: reproducing an image of content; obtaining information regarding a posture of a user based on an image of the user; determining whether the posture of the user is acceptable based on the obtained information regarding the posture of the user; and controlling reproduction of the content according to a result of the determination.

The controlling may include, when the posture of the user is not determined to be acceptable, reproducing a distorted image of the content.

The content providing method may further include: in response to reproducing the distorted image of the content, determining whether the posture of the user is acceptable; and reproducing an undistorted image of the content in response to determining that the posture of the user is acceptable.

The distorted image may include an image of the content having a change in at least one of a definition, a color tone, a chroma, a brightness, and an image form of the image of the content.

The controlling may include interrupting reproduction of the content in response to determining that the posture of the user is not acceptable.

The content providing method may further include: determining whether the posture of the user is acceptable, in response to interrupting the reproduction of the content; and reproducing the content in response to determining that the posture of the user is acceptable.

The controlling may include providing a notification message to the user in response to determining that the posture of the user is not acceptable.

The content providing method may include determining whether the posture of the user is acceptable, in response to providing the notification message; and removing the notification message in response to determining that the posture of the user is acceptable.

The information regarding the posture of the user may include information regarding a skeleton of the user, and the determining may include: comparing the information regarding the skeleton with predetermined reference information; and determining whether the posture of the user is acceptable according to a result of the comparison.

The controlling may include: dividing a content reproduction screen of the electronic device into a plurality of regions, in response to determining that the posture of the user is not acceptable; and respectively displaying the content and the image of the user in the plurality of regions.

The content providing method may further include transmitting the image of the user to a communication terminal of the user in response to determining that the posture of the user is not acceptable.

The content providing method may further include: storing the information regarding the posture of the user; and outputting the stored information regarding the posture of the user.

The content providing method may further include providing content for assessing a health of the user according to the stored information regarding the posture of the user.

The content may be content for assessing the posture of the user, and the method may further include obtaining information regarding assessment of the posture of the user based on the obtained information regarding the posture of the user.

The obtaining the information regarding the assessment of the posture of the user may include transmitting the information regarding the posture of the user to a server; and receiving, from the server, the information regarding the assessment of the posture of the user.

The content providing method may further include obtaining additional information including at least one of gesture information and voice information of the user, wherein the obtaining the information regarding the assessment of the posture of the user may include obtaining the information regarding the assessment of the posture of the user based on the additional information.

The content providing method may further include providing posture correcting content based on the information regarding the assessment of the posture of the user.

The content providing method may further include providing the posture correcting content from the electronic device to a communication terminal of the user.

According to an aspect of another exemplary embodiment, there is provided a non-transitory computer readable recording medium having embodied thereon a computer program for executing the content providing method.

According to an aspect of another exemplary embodiment, there is provided an electronic device for providing content, the electronic device including: a content provision unit configured to reproduce an image of content; a posture information obtaining unit configured to obtain information regarding a posture of a user based on an image of the user; a determination unit configured to determine whether the posture of the user is acceptable based on the information regarding the posture of the user; and a content control unit configured to control reproduction of the content according to a result of the determination of the determination unit.

According to an aspect of another exemplary embodiment, there is provided a display device including: a display unit configured to display an image of content to a user; and a controller configured to control the display unit to display the image of the content based on a posture of the user.

BRIEF DESCRIPTION OF THE DRAWINGS

The above and other aspects will become more apparent by describing in detail exemplary embodiments thereof with reference to the attached drawings, in which:

FIG. 4 is a flow chart showing a method of providing content for health assessment by using accumulated information regarding a viewing posture according to an exemplary embodiment;

FIG. 5 is a flow chart showing a method of providing posture correcting content according to an exemplary embodiment;

FIG. 10 is a schematic view for explaining a method for assessing a user's posture according to an exemplary embodiment.

DETAILED DESCRIPTION

Figure 1:
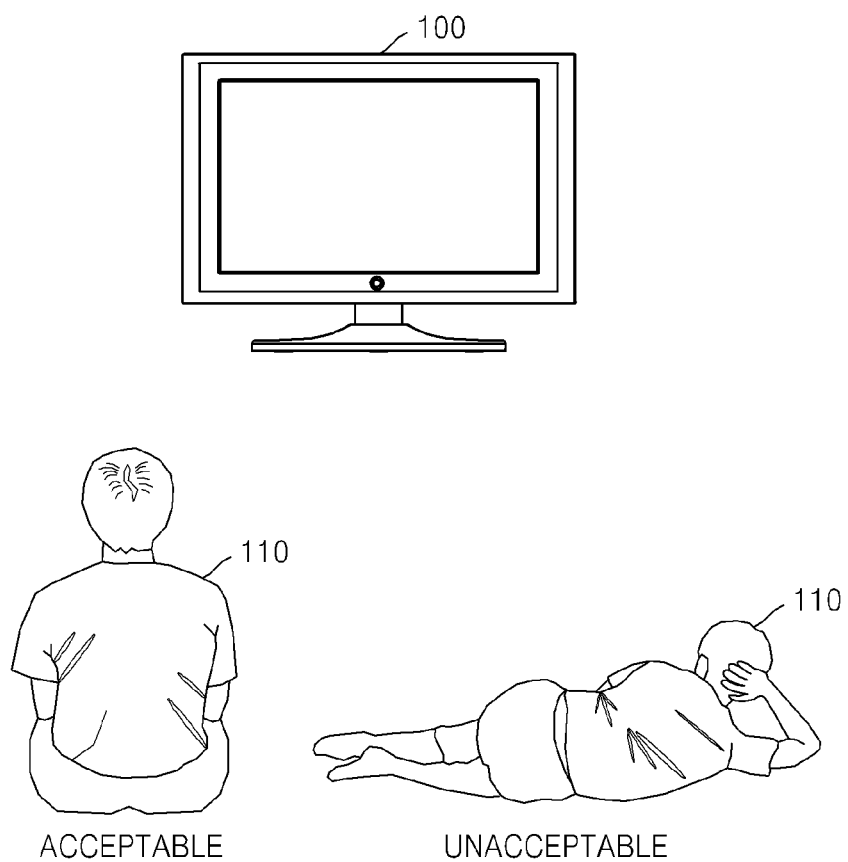
FIG. 1 is a schematic view showing a user who watches an electronic device for providing content according to a user's posture according to an exemplary embodiment.

Hereinafter, exemplary embodiments will now be described more fully with reference to the accompanying drawings. The exemplary embodiments may, however, be embodied in many different forms and should not be construed as being limited to the embodiments set forth herein; rather, these embodiments are provided so that this disclosure will be thorough and complete, and will fully convey the scope of the disclosure to those skilled in the art. For example, configuring elements that are singular forms may be executed in a distributed fashion, and also, configuring elements that are distributed may be combined and then executed. In the following description, well-known functions or constructions are not described in detail since they would obscure the disclosure with unnecessary detail. Also, throughout the specification, like reference numerals in the drawings denote like elements.

Throughout the specification, it will also be understood that when an element is referred to as being "connected to" another element, it can be directly connected to the other element, or electrically connected to the other element while intervening elements may also be present. Also, when a part "includes" or "comprises" an element, unless there is a particular description contrary thereto, the part can further include other elements, not excluding the other elements. Expressions such as "at least one of," when preceding a list of elements, modify the entire list of elements and do not modify the individual elements of the list.

FIG. 1 is a schematic view showing a user who watches an electronic device 100 for providing content according to a user's posture according to an exemplary embodiment.

According to an exemplary embodiment, the electronic device 100 may provide content to a user 110 and may control the content according to a posture of the user 110 who watches the content.

For example, the electronic device 100 may capture an image of the user 110, and when the posture of the user 110 in the image is acceptable, the electronic device 100 normally provides content. On the other hand, in an exemplary embodiment, when the posture of the user 110 is unacceptable, the electronic device 100 may distort the content change the content by controlling a content providing screen.

Here, the content providing screen or a content reproduction screen refers to controlling of content reproduction.

Figure 2:
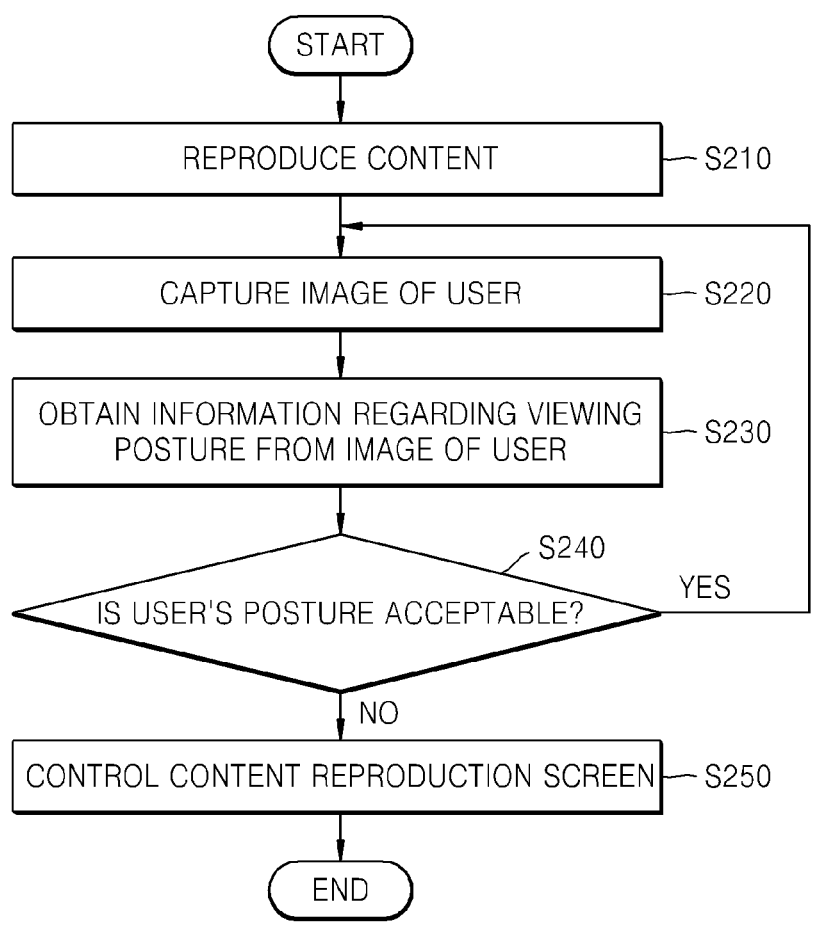
FIG. 2 is a schematic flow chart showing a content providing method according to an exemplary embodiment.

FIG. 2 is a schematic flow chart showing a content providing method according to an exemplary embodiment.

First, the electronic device 100 reproduces content (operation S210).

Here, the content is information provided to a user, and may include, for example, a video, a static image, or an audio signal. In addition, for example, the electronic device 100 may reproduce content such as a movie.

Next, the electronic device 100 generates an image by capturing a picture of the user 110 (operation S220).

Next, the electronic device 100 obtains information regarding a viewing posture from the image of the user (operation S230).

The information regarding the viewing posture is information obtained from a shape of the user 110 in the image. The information regarding the viewing posture may include, for example, a silhouette of the user 110, a skeleton, a shoulder line, and a neck line of the user 110, symmetric information, a position of eyes of the user 110, a depth of the image, and a distance between the electronic device 100 and the user 110.

Next, the electronic device 100 determines whether a posture of the user 110 is acceptable based on the information regarding the viewing posture (operation S240).

According to an exemplary embodiment, the shoulder line of the user 110 may be compared with a predetermined reference line. When an angle between the shoulder line of the user 110 and the reference line is equal to or more than a predetermined angle, it may be determined that the posture of the user 110 is unacceptable.

Figure 6:
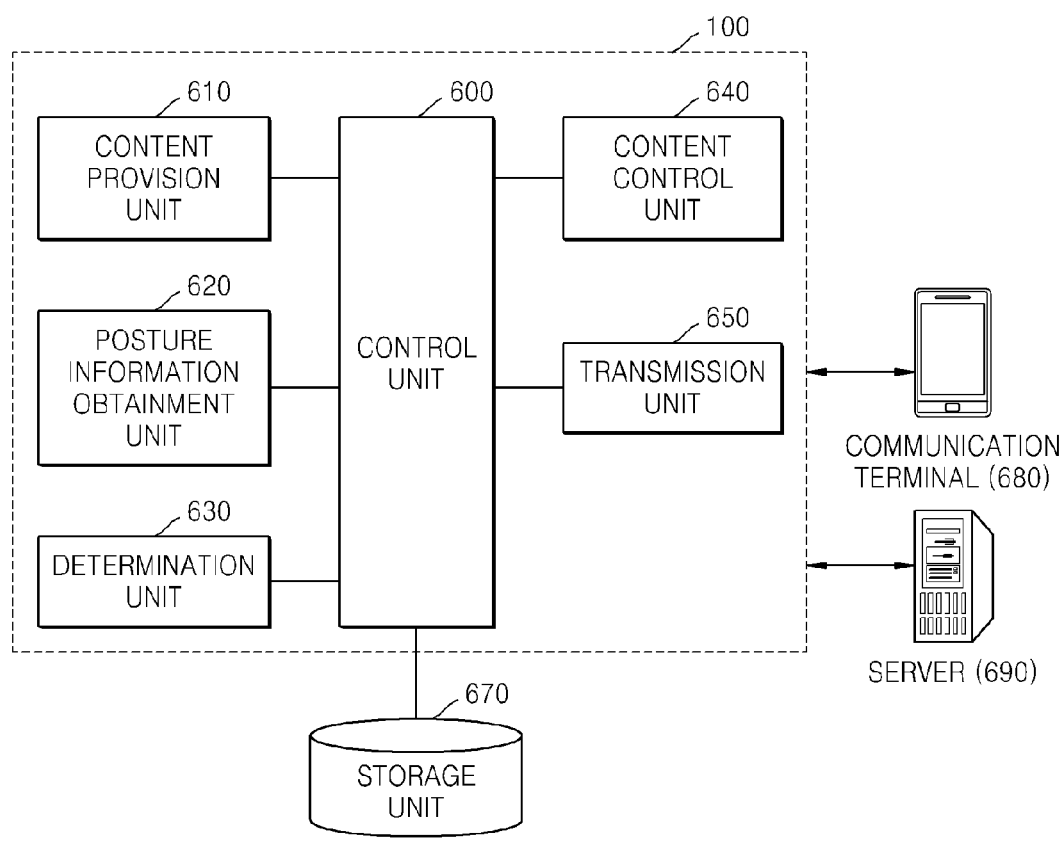
FIG. 6 is a block diagram showing a configuration of an electronic device that provides content according to an exemplary embodiment.

According to another exemplary embodiment, the electronic device 100 may transmit the image generated in operation S220 to a communication terminal 680 as shown in FIG. 6, which is communicatively connected to the electronic device 100. A user of the communication terminal 680 which receives the image from the electronic device 100 may input information regarding a reference posture to the communication terminal 680. For example, the user of the communication terminal 680 may input an outline of his or her desired posture as the reference posture. The communication terminal 680 may transfer the input information regarding the reference posture to the electronic device 100. In operation 240, the electronic device 100 may compare the information regarding the viewing posture obtained from the shape of the user 110 in the image generated in operation S220 with the reference posture to control the content reproduction screen. For example, when the information regarding the viewing posture does not correspond to the outline of the posture, i.e., the reference posture, received through the communication terminal 680, an image on the content reproduction screen may be distorted so that the content may not be normally provided. Therefore, it is possible to induce a correct posture of the user 110 by providing undistorted content only when the user 110 has the reference posture that is input to the communication terminal 680.

When the user's posture is determined to be unacceptable, the electronic device 100 controls the content reproduction screen (operation S250).

In this case, the electronic device 100 may control the content reproduction screen to assist the user 110 to correct his or her current posture into an acceptable posture.

Figure 3:
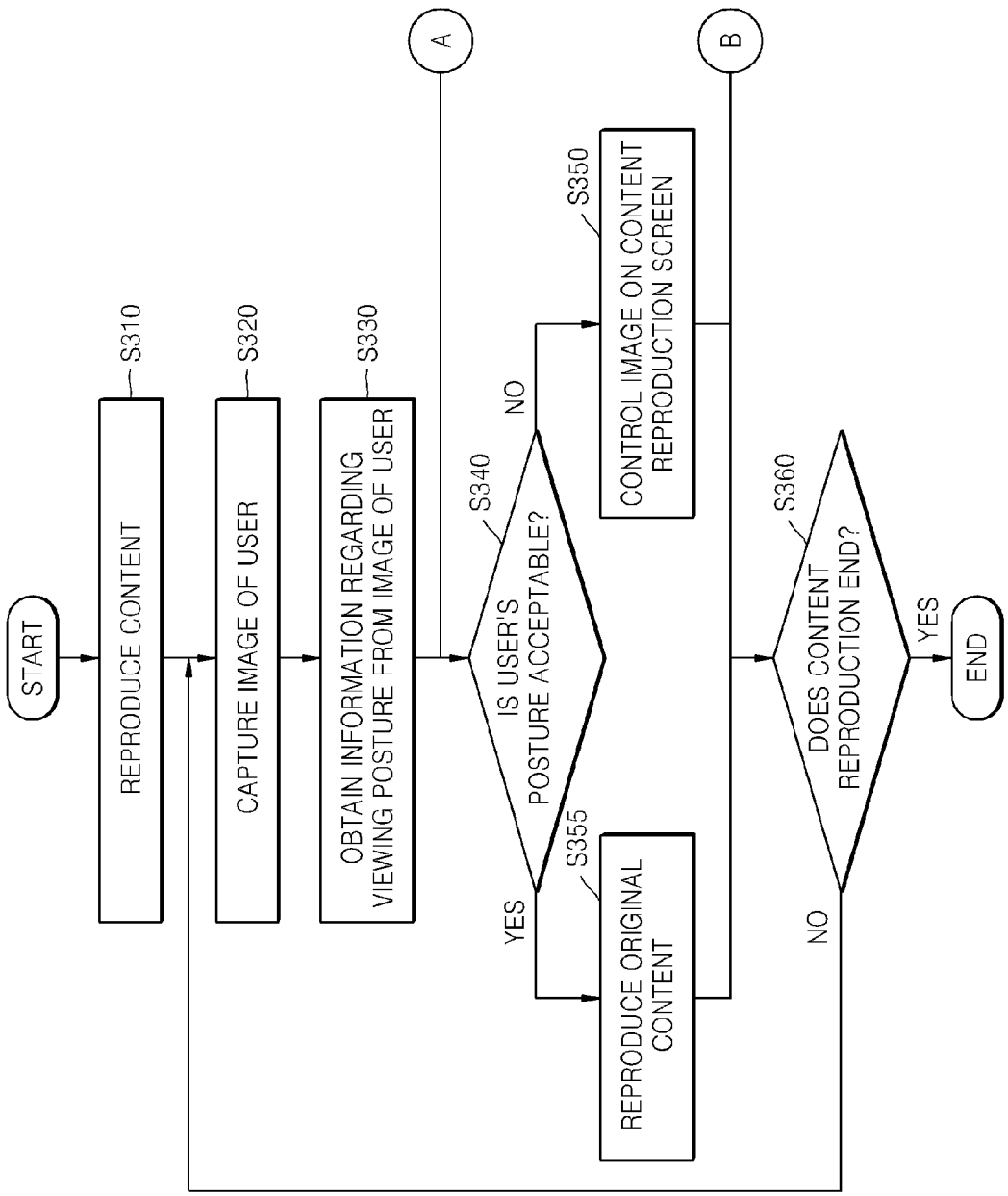
FIG. 3 is a detailed flow chart showing a content providing method according to an exemplary embodiment.

FIG. 3 is a detailed flow chart showing the content providing method according to an exemplary embodiment.

First, the electronic device 100 reproduces content (operation S310).

The content to be reproduced may include image content such as a movie.

In addition, as shown in FIG. 10, the content to be reproduced may be content for assessing health of the user.

Next, the electronic device 100 generates an image by capturing a picture of the user 110 (operation S320).

Next, information regarding a viewing posture of the user is obtained from the image of the user (operation S330).

Here, according to an exemplary embodiment, the information regarding the viewing posture may include information regarding a skeleton of the user which is obtained from the image of the user.

Next, the electronic device 100 determines whether a posture of the user 110 is acceptable based on the information regarding a viewing posture (operation S340).

The information regarding the viewing posture may include information regarding the skeleton of the user. The information regarding the skeleton of the user may include information regarding an angle of a joint, an alignment of a shoulder skeleton, and the like.

In addition, according to an exemplary embodiment, information regarding the viewing posture may include a position of the eyes, a posture of an upper body, a shoulder line, a neck line, and symmetric information of a users face obtained from the image of the user.

According to an exemplary embodiment, the electronic device 100 compares the information regarding the skeleton of the user, which is included in the information regarding the viewing posture, with reference information, and may determine whether the posture of the user 110 is acceptable according to the comparison result.

In addition, according to another exemplary embodiment, the electronic device 100 may determine whether the user's posture is inclined based on the position of the eyes, the posture of the upper body, the shoulder line, the neck line, the symmetric information of the users face, and the like. When the user's posture is inclined at an angle that is equal or more than a reference value, the electronic device 100 may determine that the user's posture is not acceptable.

In addition, according to an exemplary embodiment, when the electronic device 100 determines that the users posture is not acceptable, the electronic device 100 may transmit the image obtained by capturing an image of the user to the communication terminal 680.

For example, when the electronic device 100 determines that a posture of a child who views content is not acceptable, the electronic device 100 may transmit an image obtained by capturing a picture of the child to a predetermined communication terminal of a parent of the child to allow the parent to correct a viewing posture of the child.

Next, when the electronic device 100 determines that the users posture is not acceptable, the electronic device 100 controls an image on the content reproduction screen which is reproduced in S310 (operation S350).

In an exemplary embodiment, the image on the content reproduction screen may be distorted. For example, the electronic device 100 may output an image on the screen in which at least one of a definition, a resolution, a color tone, a chroma, and a brightness is changed, or an image layout is changed, or an image form is modified.

Figure 9A:
FIG. 9A is a schematic view showing an example in which content is reproduced in an electronic device.
Figure 9B:
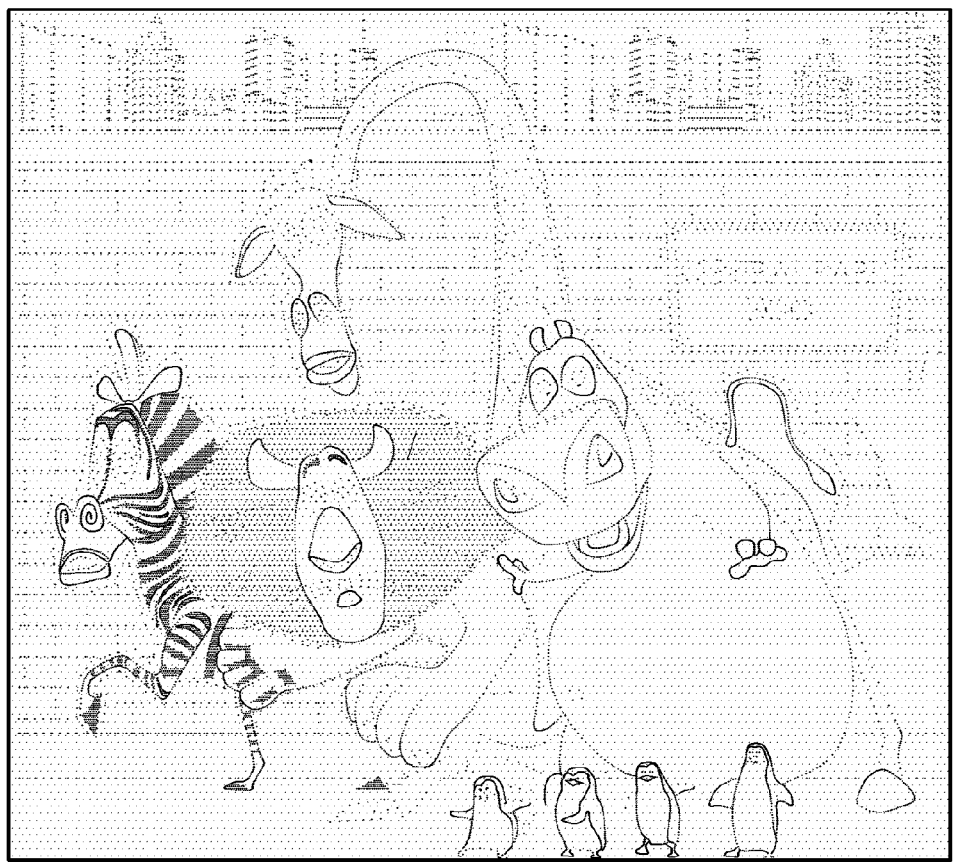
FIG. 9B is a schematic view showing an example in which resolution of a content reproduction screen of an electronic device is changed according to an exemplary embodiment.

According to an exemplary embodiment, the electronic device 100 may output an image on the content reproduction screen of which resolution is changed as shown in FIG. 9B from that of a content reproduction screen as shown in FIG. 9A.

Figure 9C:
FIG. 9C is a schematic view showing an example in which an image layout of a content reproduction screen of an electronic device is changed according to an exemplary embodiment.

According to another exemplary embodiment, the electronic device 100 may output an image layout changed as shown in FIG. 9C from that of the content reproduction screen as shown in FIG. 9A.

In addition, the electronic device 100 may interrupt display of the image on the reproduction screen.

In addition, the electronic device 100 may generate a notification message to be output to the content reproduction screen.

Figure 9D:
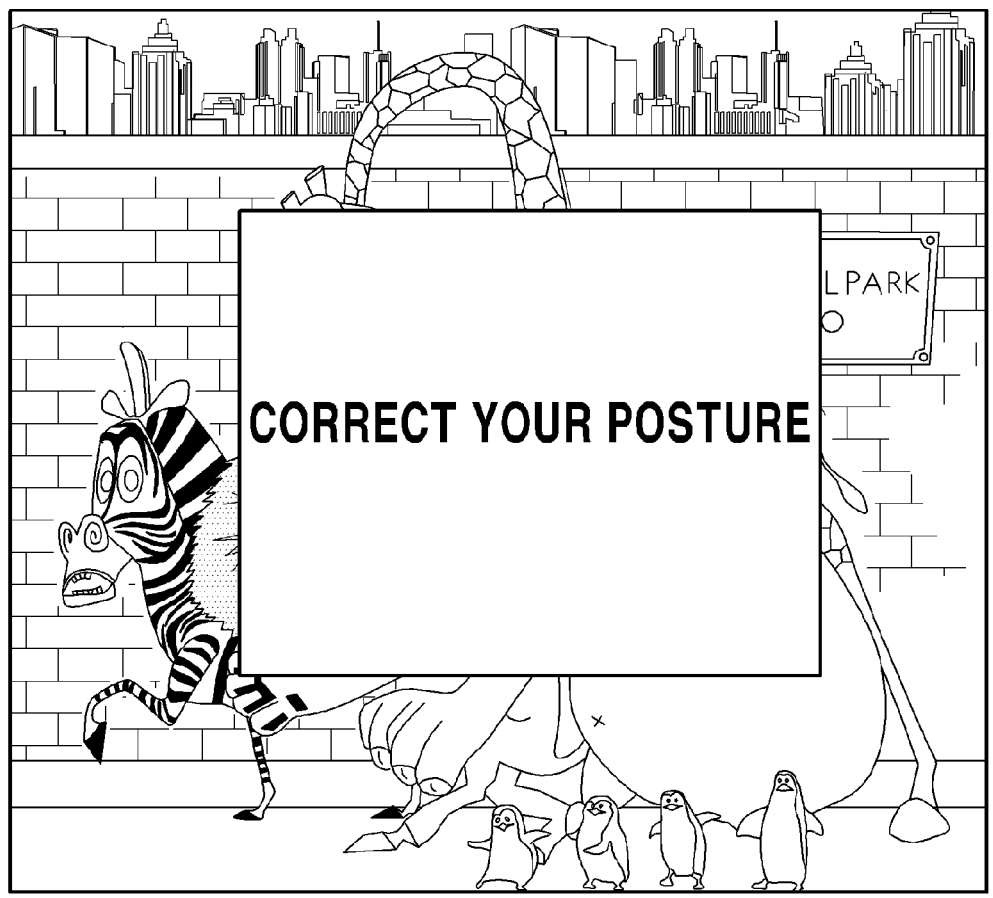
FIG. 9D is a schematic view showing an example in which a notification message is output to a content reproduction screen of an electronic device according to an exemplary embodiment.

According to an exemplary embodiment, the electronic device 100 may output the notification message as shown in FIG. 9D.

In addition, the content reproduction screen may be divided into a plurality of regions, and the content reproduction screen and the image obtained by capturing the user may be output to each of the regions.

Figure 9E:
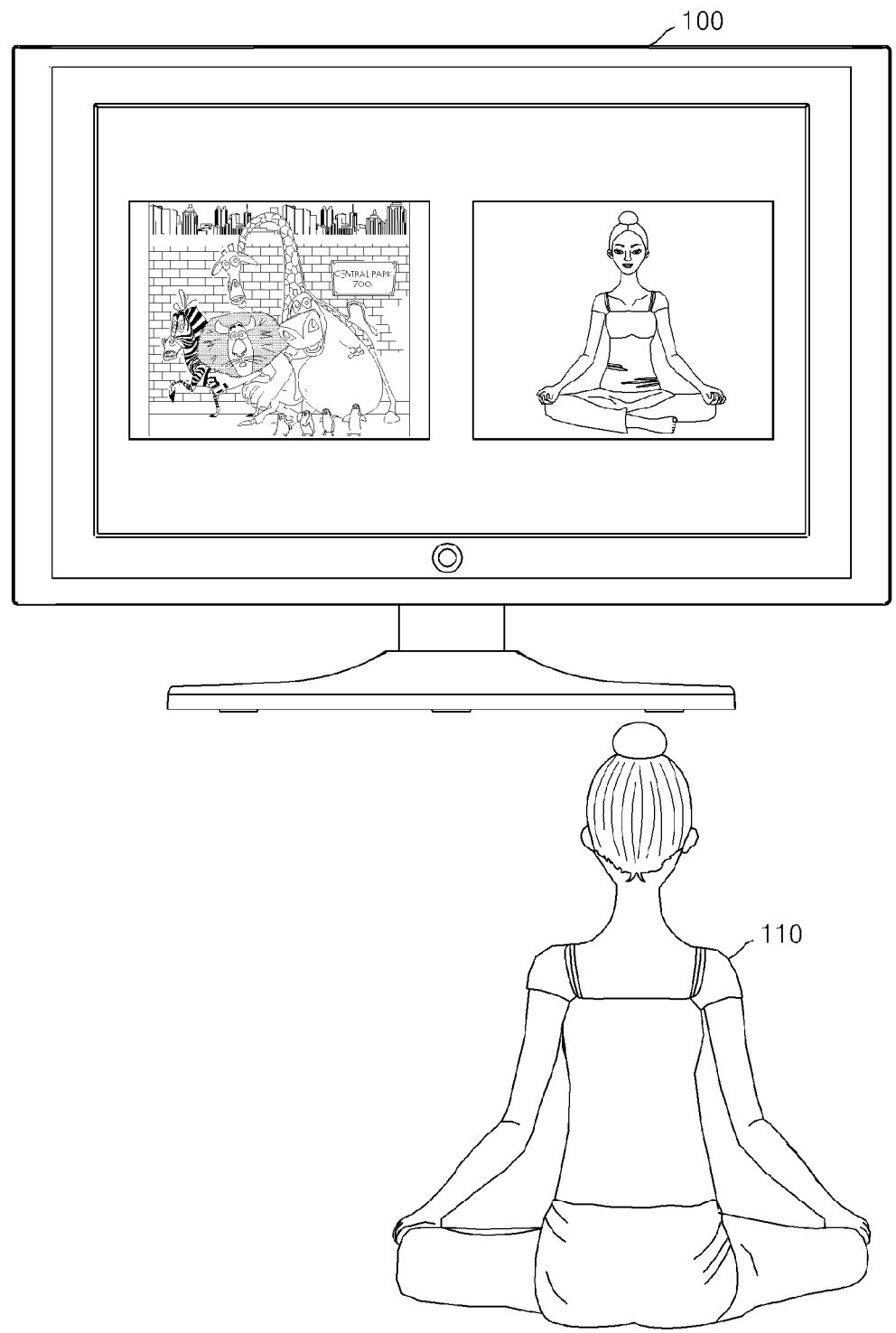
FIG. 9E is a schematic view showing an example in which a content reproduction screen of an electronic device is divided into a plurality of regions to which content and a captured image of a user are respectively output according to an exemplary embodiment.

According to an exemplary embodiment, when the user's posture is determined to be unacceptable while the image on the content reproduction screen as shown in FIG. 9A is output, the content reproduction screen may be divided as shown in FIG. 9E. The image on the content reproduction screen and the image obtained by capturing the user may be output to each of the regions.

Next, when the reproduction of content is not finished (operation S360), the electronic device 100 may capture the image of the user again (operation S320).

When the user's posture is determined to be acceptable in operation S340, original content that is reproduced in operation S310 is reproduced (operation S355).

For example, when a distorted image on the content reproduction screen is output in operation S350 and the users posture became acceptable, the original undistorted content reproduced before the distortion may be reproduced in operation S355.

In another example, when the content reproduction screen interrupts displaying content in operation S350, the content may be again reproduced on the reproduction screen in operation 355.

In still another example, when the notification message is displayed on the content reproduction screen in operation S350, the notification message may be removed from the content reproduction screen in operation 355.

In still another example, when the content reproduction screen is divided into a plurality of regions and the image on the content reproduction screen and the image obtained by capturing the user are output to each of the regions in operation S350, the image on the content reproduction screen may be output to an entire screen in operation 355.

Next, when the reproduction of the content is completed, the content providing method ends (operation S360).

FIG. 4 is a flow chart showing a method of providing content for health assessment by using accumulated information regarding a viewing posture according to an exemplary embodiment.

First, the electronic device 100 may accumulate the information regarding the viewing posture which is obtained in operation S330 and store the information.

In addition, the electronic device 100 may calculate a statistical value with respect to the accumulated information regarding the viewing posture.

For example, the electronic device 100 may calculate the number of receiving of information regarding the viewing posture that is determined to be unacceptable by using the accumulated information regarding the viewing posture. In other words, the electronic device 100 may calculate the number of receiving of information regarding the viewing posture that is determined to be unacceptable from the accumulated information regarding the viewing posture during a predetermined period of time, e.g., one hour.

In another example, the electronic device 100 may obtain a statistic about whether the posture is not acceptable by determining which body part such as a shoulder or a waist is not in a correct posture by using the accumulated information regarding a viewing posture. In other words, it is possible to classify information regarding a viewing posture that is determined to be unacceptable depending on whether an unacceptable viewing posture is due to, for example, an inclined shoulder, a waist posture, or a neck posture and calculate the number of information regarding a viewing posture according to the classification.

Next, the electronic device 100 may output the information regarding a viewing posture which is accumulated and stored (operation S420).

For example, it is possible to output to a screen the information regarding a viewing posture that is accumulated and stored in a form of a table.

Accordingly, the electronic device 100 may provide content, e.g., content for health assessment, according to the information regarding a viewing posture which is accumulated and stored.

According to an exemplary embodiment, when the number of information regarding a viewing posture that is determined to be unacceptable is equal to or higher than a predetermined value, the content for health assessment may be provided.

For example, when the number of information regarding a viewing posture that is determined to be unacceptable during the content reproduction is equal to or higher than 10, it is possible to instruct the user to adopt a specific posture as shown in FIG. 10, and an image of the user in the new posture is captured, thereby providing the content for assessing the user's health.

Here, according to an exemplary embodiment, it is possible to allow the user to select content to be reproduced from a list of contents for health assessment, or the contents for health assessment may be immediately reproduced.

FIG. 5 is a flow chart showing a method of providing posture correcting content according to an exemplary embodiment.

First, the electronic device 100 obtains information regarding a users posture (operation S510).

Here, the content for assessing the user's health may be reproduced during operation 510.

For example, as shown in FIG. 10, the information regarding a users posture may be obtained by suggesting the user to adopt a specific posture and by capturing an image of the user in the suggested posture. In other words, the posture of the user in the image is compared with the reference posture, and information such as flexibility, the alignment of a shoulder line, and a degree of bending in a spine of the user may be obtained according to the comparison result.

In addition, according to an exemplary embodiment, the electronic device 100 may obtain gesture or voice information of the user as additional information, and may obtain information regarding a users posture based on the information regarding a viewing posture and the additional information.

For example, as shown in FIG. 10, the information regarding a users posture may include a posture that is difficult for the user to adopt determined by using, as additional information, a sound that the user produces when the user adopts a specific posture.

Next, the electronic device 100 may provide a posture correcting content according to the information regarding a user's posture (operation S520). For example, the electronic device 100 may compare the information regarding a user's posture with reference information. According to the comparison result, for example, when a users waist posture is determined to be unacceptable, a posture correcting content with respect to the user's waist may be reproduced.

According to an exemplary embodiment, it is possible to allow the user to select the posture correcting content to be reproduced from a list of posture correcting contents, or the posture correcting content may be immediately reproduced.

Next, the electronic device 100 may transmit the posture correcting content to another electronic device so that the user 110 may receive the posture correcting content through another electronic device (operation S530).

For example, it is possible to allow the user to receive the posture correcting content from a TV through a tablet PC.

FIG. 6 is a block diagram showing a configuration of the electronic device 100 that provides content according to an exemplary embodiment.

The electronic device 100 according to an exemplary embodiment may include a content provision unit 610 that reproduces content to be provided to the user 110, a posture information obtaining unit 620 that captures an image of the user 110 who views the content and obtains information regarding a viewing posture of the user 110 from the image of the user, a determination unit 630 that determines whether a posture of the user is acceptable based on the information regarding a viewing posture of the user, a content control unit 640 that controls a content reproduction screen according to the determination result of the determination unit 630, and a control unit 600 that controls each unit of the electronic device 100.

In addition, the electronic device 100 may further include a transmission unit 650 that transmits the image on the content reproduction screen or the image obtained by capturing the image of the user to the communication terminal 680, and a storage unit 670 that stores the information regarding a viewing posture of the user. The posture information obtaining unit 620 may obtain information regarding a posture of the user 110.

The content provision unit 610 reproduces and outputs content to the user 110.

According to an exemplary embodiment, the content provision unit 610 may output content that is controlled by the content control unit 640. The content may be distorted by the content control unit 640.

According to another exemplary embodiment, when the content provision unit 610 determines that the user's posture is not acceptable, the content provision unit 610 may stop the content from being reproduced.

In addition, when the provision unit 610 determines that the user's posture is acceptable, the content provision unit 610 may reproduce the stopped content again.

According to an exemplary embodiment, when the determination unit 630 determines that the user's posture is not acceptable, the content provision unit 610 may output a notification message to the content reproduction screen. In addition, when the determination unit 630 later determines that the posture of the user 110 becomes acceptable, the notification message displayed on the content reproduction screen may be removed.

According to another exemplary embodiment, when the determination unit 630 determines that the user's posture is not acceptable, the content reproduction screen may be divided into a plurality of regions, and the content and the image obtained by taking a picture of the user 110 may be displayed in each of the regions.

In addition, according to another exemplary embodiment, the content provision unit 610 may output the information regarding a viewing posture of the user which is accumulated and stored.

Here, the content provision unit 610 may provide content for assessing the user's health according to the information regarding a viewing posture of the user which is accumulated and stored.

For example, when the number of receiving of information regarding a viewing posture that is determined to be unacceptable is equal to or higher than a predetermined number, the content for assessing the users health may be provided.

In addition, according to another exemplary embodiment, a posture correcting content may be provided based on the information regarding a viewing posture which is obtained by the posture information obtaining unit 620.

For example, when the information regarding a viewing posture includes information indicating that a waist posture of the user 110 is not acceptable, a waist posture correcting content may be provided.

The posture information obtaining unit 620 obtains the information regarding a viewing posture of the user 110 by capturing an image of the user 110 who views the content.

The determination unit 630 determines whether the users posture is acceptable based on the information regarding a viewing posture of the user.

Here, the information regarding a viewing posture includes information regarding a users skeleton, and the determination unit 630 may compare the information regarding a user's skeleton with predetermined reference information and may determine whether the users posture is acceptable according to the comparison result.

In addition, according to another exemplary embodiment, the content provision unit 610 may provide the posture correcting content based on the information regarding a viewing posture.

The content control unit 640 controls a content reproduction screen according to the determination result of the determination unit 630.

According to an exemplary embodiment, when the content control unit 640 determines that the posture of the user 110 is not acceptable, the content control unit 640 may control the content provision unit 610 to provide distorted content to be reproduced.

Here, the content control unit 640 may change at least one of, for example, the definition, the color tone, the chroma, the brightness, and the image form of the content to distort the content.

In addition, while the content provision unit 610 reproduces the distorted content, when the determination unit 630 determines that the posture of the user 110 is acceptable, the content control unit 640 may stop the distortion with respect to the content.

The transmission unit 650 may transmit the image on the content reproduction screen or the image obtained by capturing an image of the user to the communication terminal 680.

According to an exemplary embodiment, when the determination unit 630 determines that the user's posture is not acceptable, the transmission unit 630 may transmit the image obtained by capturing the user to the communication terminal 680.

According to another exemplary embodiment, the posture information obtaining unit 620 may obtain the information regarding a posture of the user 110.

For example, it is possible to allow content for assessing a users waist posture to be reproduced by the content provision unit 610, and it is also possible to instruct the user to adopt a posture according to the content for measuring the posture provided to the user. Here, the posture information obtaining unit 620 may obtain information regarding the posture adopted by the user 110. The content provision unit 610 may reproduce the posture correcting content based on the information regarding the posture. For example, according to results obtained by comparing the information regarding the posture with predetermined reference information, when the users waist posture is determined to be unacceptable, a posture correcting content with respect to the waist may be reproduced.

According to an exemplary embodiment, the posture information obtaining unit 620 may transmit the information regarding a viewing posture to a server 690. The server 690 may transmit, to the electronic device 100, information regarding a posture generated based on the transmitted information regarding a viewing posture.

According to another exemplary embodiment, the posture information obtaining unit 620 may obtain information regarding a user's posture based on additional information obtained by an additional information obtaining unit (not shown). For example, when a user waves his or her hand or when a user produces a sound while attempting to perform a specific operation, the specific operation may be determined to be difficult for the user to perform. The information regarding a user's posture may be generated according to the operation that is difficult for the user to perform.

Figure 8:
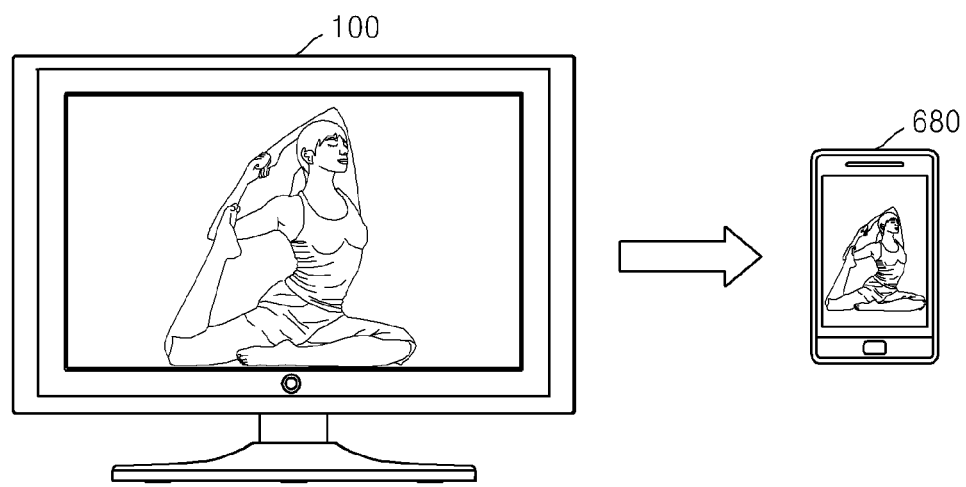
FIG. 8 is a schematic view showing an example in which a posture correcting content is provided to another device according to an exemplary embodiment.

According to an exemplary embodiment, the transmission unit 650 may transmit the posture correcting content provided by the content provision unit 610 to the communication terminal 680 as shown in FIG. 8.

The storage unit 670 may store the information regarding a viewing posture of the user 110.

For example, the information regarding a viewing posture of the user 110 is accumulated and stored, and the number of receiving of information regarding a viewing posture that is determined to be unacceptable by the determination unit 630 while the user 110 watches the content may be accumulated and stored in the form of a table.

Although not shown in the drawing, in an exemplary embodiment, the electronic device 100 may further include the additional information obtaining unit that obtains additional information may include at least one of gesture and voice information of the user 110.

For example, the additional information obtaining unit may detect a user's gesture from an image obtained by capturing a picture of the user with a camera, or may receive the input of a user's voice via a microphone.

Figure 7:
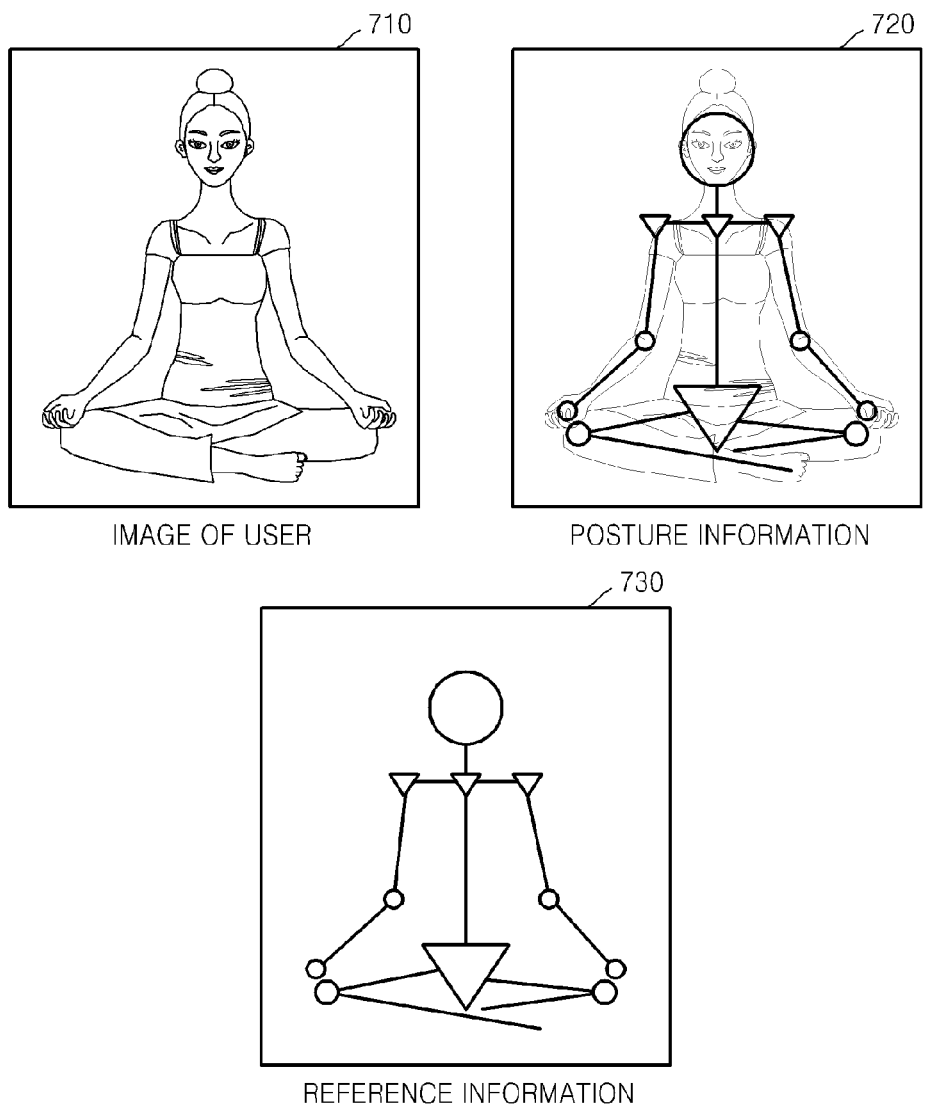
FIG. 7 is a schematic view for explaining a method of determining whether a user's posture is acceptable according to an exemplary embodiment.

FIG. 7 is a schematic view for explaining a method of determining whether a user's posture is acceptable according to an exemplary embodiment.

The electronic device 100 obtains posture information 720 from an image 710 that is obtained by, for example, photographing the user 110. Here, the posture information 720 may be information regarding a viewing posture of a user.

According to an exemplary embodiment, as shown in FIG. 7, a joint or a shape of a skeleton of the user 110 may be recognized from information regarding an outline and a depth of the image 710. The information regarding the viewing posture 720 may include information regarding the position of the recognized joint or the shape of the skeleton of the user 110.

The electronic device 100 may compare the obtained posture information 720 regarding the viewing posture with predetermined reference information 730 to determine whether a posture of the user 110 is acceptable.

FIG. 8 is a schematic view showing an example in which the posture correcting content is provided to another device according to an exemplary embodiment.

According to an exemplary embodiment, the electronic device 100 may transmit content to be reproduced to another terminal of the user, e.g., the communication terminal 680.

For example, while posture correcting content, e.g., content related to yoga may be reproduced on a TV, the user may control the same content related to yoga to be reproduced on, for example, a portable terminal of the user. Therefore, the user may use the posture correcting content in a place where a TV is not provided.

FIG. 9A is a schematic view showing an example in which content is reproduced in the electronic device 100.

As shown in FIG. 9A, the electronic device 100 may reproduce content including an image.

FIG. 9B is a schematic view showing an example in which resolution of a content reproduction screen of the electronic device 100 is changed according to an exemplary embodiment.

As shown in FIG. 9B, when a posture of a user is determined to be unacceptable, the electronic device 100 may restrict use of content by changing the resolution of the content reproduction screen.

FIG. 9C is a schematic view showing an example in which an image layout of the content reproduction screen of the electronic device 100 is changed according to an exemplary embodiment.

As shown in FIG. 9C, when a users posture is determined to be unacceptable, the electronic device 100 may divide the content reproduction screen and may change and reproduce the image layout of the divided screen to restrict the use of the content.

FIG. 9D is a schematic view showing an example in which a notification message is output to the content reproduction screen of the electronic device 100 according to an exemplary embodiment.

As shown in FIG. 9D, when a users posture is determined to be unacceptable, the electronic device 100 may output the notification message to the content reproduction screen to notify that the user's posture is not acceptable.

FIG. 9E is a schematic view showing an example in which the content reproduction screen of the electronic device 100 is divided into a plurality of regions to which an image of content and an image that is obtained by capturing a user are respectively output according to an exemplary embodiment.

As shown in FIG. 9E, when a users posture is determined to be unacceptable, the electronic device 100 may output both the image of the content and the image that is obtained by capturing the user.

FIG. 10 is a schematic view for explaining a method for assessing a user's posture according to an exemplary embodiment.

According to an exemplary embodiment, the electronic device 100 may provide reference posture content 1000.

When the user 110 adopts a posture according to the provided reference posture content 1000, the electronic device 100 may capture an image 1010 of the user.

The electronic device 100 may obtain information regarding a posture of the user 110 based on the image 1010. The information regarding a posture of the user 110 and the reference posture content 1000 may be used to assess the user's posture, i.e., whether the user's posture is acceptable.

The one or more exemplary embodiments may be embodied as a non-transitory recording medium, e.g., a program module to be executed in computers, which include computer-readable commands. The non-transitory recording medium may include any usable medium that may be accessed by computers, volatile and non-volatile medium, and detachable and non-detachable medium. Also, the non-transitory recording medium may include a computer storage medium and a communication medium. The computer storage medium includes all of volatile and non-volatile medium, and detachable and non-detachable medium which are designed to store information including computer readable commands, data structures, program modules or other data. The communication medium includes computer-readable commands, a data structure, a program module, and other transmission mechanism, and includes other information transmission mediums.

Although a few exemplary embodiments have been shown and described, it will be understood by those of ordinary skill in the art that various changes in form and details may be made therein without departing from the spirit and scope of the inventive step as defined by the following claims.

What is claimed is:

1. A content providing method in an electronic device, the method comprising:
reproducing an image of content;
obtaining information regarding a posture of a user based on an image of the user;
determining whether the posture of the user is acceptable based on the obtained information regarding the posture of the user; and
controlling reproduction of the content according to a result of the determination,
wherein the content comprises an image that is independent of the image of the user, and
wherein the controlling comprises:
if the posture of the user is acceptable, reproducing a normal image of the content, and if the posture of the user is not acceptable, reproducing a distorted image of the content, and
wherein the distorted image has lower visibility than the normal image.

2. The content providing method of claim 1, further comprising:
in response to reproducing the distorted image of the content, determining whether the posture of the user is acceptable; and
reproducing an undistorted image of the content in response to determining that the posture of the user is acceptable.

3. The content providing method of claim 1, wherein the distorted image comprises an image of the content having a change in at least one of a color definition, a color tone, a chroma, a brightness, and an image form of the image of the content.

4. The content providing method of claim 1, wherein the controlling comprises interrupting reproduction of the content in response to determining that the posture of the user is not acceptable.

5. The content providing method of claim 4, further comprising:
determining whether the posture of the user is acceptable, in response to interrupting the reproduction of the content; and
reproducing the content according to a result of the determining.

6. The content providing method of claim 1, wherein the controlling comprises providing a notification message including texts to the user in response to determining that the posture of the user is not acceptable.

7. The content providing method of claim 6, further comprising:
determining whether the posture of the user is acceptable, in response to providing the notification message; and
removing the notification message in response to determining that the posture of the user is acceptable.

8. The content providing method of claim 1, wherein the information regarding the posture of the user comprises information regarding a skeleton of the user, and wherein the determining comprises:
comparing the information regarding the skeleton with predetermined reference information; and
determining whether the posture of the user is acceptable according to a result of the comparison.

9. The content providing method of claim 1, wherein the controlling comprises:
dividing a content reproduction screen of the electronic device, in response to determining that the posture of the user is not acceptable; and
displaying the content in a divided area of the content reproduction screen.

10. The content providing method of claim 1, further comprising transmitting the image of the user to a communication terminal of the user in response to determining that the posture of the user is not acceptable.

11. The content providing method of claim 1, further comprising:
storing the information regarding the posture of the user; and
outputting the stored information regarding the posture of the user.

12. The content providing method of claim 11, further comprising providing content for assessing a health of the user according to the stored information regarding the posture of the user.

13. The content providing method of claim 1, wherein the content is content for assessing the posture of the user, and the method further comprises obtaining information regarding assessment of the posture of the user based on the obtained information regarding the posture of the user.

14. The content providing method of claim 13, wherein the obtaining the information regarding the assessment of the posture of the user comprises:
transmitting the information regarding the posture of the user to a server; and
receiving, from the server, the information regarding the assessment of the posture of the user.

15. The content providing method of claim 13, further comprising obtaining additional information comprising at least one of gesture information and voice information of the user, wherein the obtaining the information regarding the assessment of the posture of the user comprises obtaining the information regarding the assessment of the posture of the user based on the additional information.

16. The content providing method of claim 13, further comprising providing posture correcting content based on the information regarding the assessment of the posture of the user.

17. The content providing method of claim 13, further comprising providing the posture correcting content from the electronic device to a communication terminal of the user.

18. A non-transitory computer readable recording medium having embodied thereon a computer program for executing the method of claim 1.

19. An electronic device for providing content, the electronic device comprising:
a display configured to display an image of content;
a controller configured to obtain information regarding a posture of a user based on an image of the user, determine whether the posture of the user is acceptable based on the information regarding the posture of the user, and control reproduction of the content according to a result of the determination;
wherein the content comprises an image that is independent of the image of the user,
wherein the controller reproduces a normal image of the content when the posture of the user is acceptable, and reproduces a distorted image of the content when the posture of the user is not acceptable, and
wherein the distorted image has lower visibility than the normal image.

20. The electronic device of claim 19, wherein, when the controller determines that the posture of the user is acceptable in response to reproduction of the distorted content, and reproduces an undistorted image of the content.

21. The electronic device of claim 19, wherein the distorted image comprises an image of the content having a change in at least one of a color definition, a color tone, a chroma, a brightness, and an image form of the image of the content.

22. The electronic device of claim 19, wherein, when the controller determines that the posture of the user is not acceptable, the controller interrupts reproduction of the content.

23. The electronic device of claim 22, wherein, when the controller determines that the posture of the user is acceptable, the controller reproduces the content.

24. The electronic device of claim 19, wherein, when the controller determines that the posture of the user is not acceptable, the display outputs a notification message including texts to a content reproduction screen.

25. The electronic device of claim 24, wherein, when the controller determines that the posture of the user is acceptable, the controller removes the notification message displayed on the content reproduction screen.

26. The electronic device of claim 19, wherein the information regarding the posture of the user comprises information regarding a skeleton of the user, and the controller compares the information regarding the skeleton with predetermined reference information and determines whether the posture of the user is acceptable according to a result of the comparison.

27. The electronic device of claim 19, wherein, when the controller determines that the posture of the user is not acceptable, the controller divides a content reproduction screen and the display displays the content in a divided area of the content reproduction screen.

28. The electronic device of claim 19, further comprising a communication interface configured to transmit the image of the user to a communication terminal of the user when the controller determines that the posture of the user is not acceptable.

29. The electronic device of claim 19, further comprising a storage unit configured to store the information regarding the posture of the user, wherein the display outputs the stored information regarding the posture of the user.

30. The electronic device of claim 29, wherein the controller provides content for assessing health of the user according to the information regarding the posture of the user which is accumulated and stored.

31. The electronic device of claim 19, wherein the content is content for assessing the posture of the user, and the controller obtains information regarding assessment of the posture of the user based on the obtained information regarding the posture of the user.

32. The electronic device of claim 31, wherein the electronic device further comprises a communication interface configured to transmit the information regarding the posture of the user to a server, and receive, from the server, the information regarding the assessment of the posture of the user.

33. The electronic device of claim 31, wherein the controller obtains additional information comprising at least one of gesture information and voice information of the user, and the controller obtains the information regarding the assessment of the posture of the user based on the additional information obtained by the controller.

34. The electronic device of claim 31, wherein the display displays a posture correcting content based on the information regarding the assessment of the posture of the user.

35. The electronic device of claim 34, wherein the communication interface provides the posture correcting content to a communication terminal of the user.

36. A display device comprising:
a display configured to display an image of content to a user; and
a controller configured to obtain information regarding a posture of the user from an image of the user, and control the display to display the image of the content based on the posture of the user,
wherein the controller controls the display to display a distorted image of the content when the posture of the user is not determined to be acceptable and display a normal image of the content when the posture of the user is determined to be acceptable, and
wherein the distorted image being an image that is independent of the image of the user, and the distorted image has lower visibility than the normal image.

37. The display device of claim 36, wherein the distorted image comprises an image of the content having a change in at least one of a color definition, a color tone, a chroma, a brightness, and an image form of an image of the image of the content.

* * * * *